(12) United States Patent
 Militello

(10) Patent No.: US 11,278,647 B2
(45) Date of Patent: Mar. 22, 2022

(54) LUBRICIOUS COATING FOR MEDICAL DEVICE

(71) Applicant: Surmodics, Inc., Eden Prairie, MN (US)

(72) Inventor: Mike Militello, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 655 days.

(21) Appl. No.: 15/474,601

(22) Filed: Mar. 30, 2017

(65) Prior Publication Data

US 2017/0281831 A1 Oct. 5, 2017

Related U.S. Application Data

(60) Provisional application No. 62/316,186, filed on Mar. 31, 2016.

(51) Int. Cl.
 *A61L 29/08* (2006.01)
 *A61L 29/14* (2006.01)

(52) U.S. Cl.
 CPC ............. *A61L 29/085* (2013.01); *A61L 29/14* (2013.01); *A61L 2400/10* (2013.01); *A61L 2420/02* (2013.01)

(58) Field of Classification Search
 CPC ........ C08L 39/06; A61L 29/04; A61L 29/041; A61L 29/049; A61L 29/085; A61L 29/14; A61L 2400/10; A61L 31/10; A61L 2420/02; A61M 25/0009; A61M 25/0045; A61M 2025/0046; A61M 2025/0047; A61M 2025/0048; A61M 2025/0056; A61M 2025/0057; A61M 2025/1088

USPC .......................................... 604/19, 172, 265
See application file for complete search history.

(56) References Cited

U.S. PATENT DOCUMENTS

| 4,979,959 | A | 12/1990 | Guire |
| 5,002,582 | A | 3/1991 | Guire et al. |
| 5,061,424 | A | 10/1991 | Karimi et al. |
| 5,263,992 | A | 11/1993 | Guire |
| 5,382,234 | A | 1/1995 | Cornelius et al. |
| 5,414,075 | A | 5/1995 | Swan et al. |

(Continued)

FOREIGN PATENT DOCUMENTS

| WO | 2003055611 A1 | 7/2003 |
| WO | 2008104573 A2 | 9/2008 |

(Continued)

OTHER PUBLICATIONS

The Heath Encyclopedia website published online by the University of Rochester Medical Center at https://www.urmc.rochester.edu/encyclopedia/content.aspx? Contenttypeid=167&contentid=bicarbonate (Year: 2020).*

(Continued)

*Primary Examiner* — Lee E Sanderson
(74) *Attorney, Agent, or Firm* — Kagan Binder, PLLC

(57) ABSTRACT

Embodiments of the disclosure include lubricious coatings. In an embodiment the disclosure includes a lubricious coating for a medical device including an acrylic acid polymer, an acrylamide copolymer comprising at least one photoreactive group, and a cross-linking agent comprising at least two photoreactive groups. The coating can be used on a catheter surface to facilitate its movement in the body.

23 Claims, 2 Drawing Sheets

(56) References Cited

U.S. PATENT DOCUMENTS

| | | | |
|---|---|---|---|
| 5,512,329 | A | 4/1996 | Guire et al. |
| 5,571,089 | A | 11/1996 | Crocker |
| 5,637,460 | A | 6/1997 | Swan et al. |
| 5,714,360 | A | 2/1998 | Swan et al. |
| 5,776,101 | A | 7/1998 | Goy |
| 5,807,331 | A | 9/1998 | den Heijer et al. |
| 5,858,653 | A | 1/1999 | Duran et al. |
| 5,882,336 | A | 3/1999 | Janacek |
| 6,156,345 | A | 12/2000 | Chudzik et al. |
| 6,394,995 | B1 | 5/2002 | Solar et al. |
| 6,517,515 | B1 | 2/2003 | Eidenschink |
| 6,623,504 | B2 | 9/2003 | Vrba et al. |
| 7,772,393 | B2 | 8/2010 | Guire et al. |
| 8,487,137 | B2 | 7/2013 | Guire et al. |
| 8,513,320 | B2 | 8/2013 | Rooijmans |
| 8,809,411 | B2 | 8/2014 | Rooijmans |
| 8,889,760 | B2 | 11/2014 | Kurdyumov et al. |
| 9,173,974 | B2 | 11/2015 | Gome et al. |
| 9,321,030 | B2 | 4/2016 | Sukhishvili et al. |
| 9,321,872 | B2 | 4/2016 | Minagawa |
| 9,393,589 | B2 | 7/2016 | Olmeijer et al. |
| 9,550,011 | B2 | 1/2017 | Xie |
| 2001/0011165 | A1 | 8/2001 | Engelson et al. |
| 2008/0213334 | A1 | 9/2008 | Lockwood et al. |
| 2009/0123519 | A1* | 5/2009 | Rolfes ................ A61K 9/1641 424/423 |
| 2010/0198168 | A1* | 8/2010 | Rooijmans ............ A61L 29/085 604/265 |
| 2011/0059874 | A1 | 3/2011 | Rooijmans et al. |
| 2011/0144373 | A1 | 6/2011 | Swan et al. |
| 2011/0245367 | A1* | 10/2011 | Kurdyumov .......... A61L 17/145 523/113 |
| 2012/0077049 | A1 | 3/2012 | Lin |
| 2012/0149934 | A1 | 6/2012 | Kurdyumov |
| 2013/0143056 | A1 | 6/2013 | Swan et al. |
| 2013/0197433 | A1* | 8/2013 | Babcock ............... A61L 27/34 604/103.02 |
| 2013/0261566 | A1* | 10/2013 | Lockwood ............ B05D 3/067 604/264 |
| 2013/0337147 | A1 | 12/2013 | Chappa et al. |
| 2014/0162083 | A1* | 6/2014 | Kurdyumov ........... A61L 31/14 428/524 |
| 2014/0193474 | A1* | 7/2014 | Babcock ............... A61L 29/14 424/422 |
| 2015/0352259 | A1 | 12/2015 | Rooijmans et al. |
| 2016/0053063 | A1 | 2/2016 | Schroter et al. |
| 2016/0310643 | A1 | 10/2016 | Dias et al. |

FOREIGN PATENT DOCUMENTS

| | | |
|---|---|---|
| WO | 2011123441 A1 | 10/2011 |
| WO | 2014107670 A1 | 7/2014 |

OTHER PUBLICATIONS

Khutoryanskiy et al., (2009) "Hydrogen-Bonded Interpolymer Complexes, pH- and Ionic Strength Effects on Interpolymer Complexation Via Hydrogen-Bonding", World Scientific Publishing Co., Pte. Ltd., Chapter 1, pp. 1-7.

Bumbu et al., (2009) "Hydrogen-Bonded Interpolymer Complexes, Interpolymer Complexes Containing Copolymers", World Scientific Publishing Co., Chapter 7, pp. 173-200.

* cited by examiner

LUBRICIOUS COATING FOR MEDICAL DEVICE

CROSS-REFERENCE TO RELATED APPLICATION

The present non-provisional application claims the benefit of commonly owned provisional Application have Ser. No. 62/316,186, filed on Mar. 31, 2016, entitled LUBRICIOUS COATING FOR MEDICAL DEVICE, which Application is incorporated herein by reference in its entirety.

FIELD

The present disclosure relates to lubricious coatings. More specifically, the present disclosure relates to lubricious medical device coatings

BACKGROUND

Medical devices include, amongst others, those that are chronically implanted, devices that are transitorily implanted, and those that not implanted at all. Many types of medical devices are enhanced by reducing the friction between the device and the environment that surrounds the medical device, particularly during insertion of a device. One example is catheters that are inserted, at least transitorily, into the body of a subject. Reduction of friction can lead to enhanced patient comfort, procedural ease for the care provider, reduced chances for infection, as well as reduced tissue disruption, amongst other benefits. One approach to reducing the friction between a medical device and the environment surrounding the medical device is to apply a lubricious coating onto the medical device.

SUMMARY OF THE INVENTION

Embodiments of the invention are directed towards lubricious coatings for medical devices, methods of forming the coatings, and using the coated medical devices.

In one embodiment the invention provides a medical device comprising a lubricious coating that has a coated layer comprising a first polymer that is an acrylic acid polymer, a second polymer that is an acrylamide copolymer comprising at least one photoreactive group, and a cross-linking agent comprising at least two photoreactive groups, wherein the coated layer is in contact with a medical device surface and also configured to contact a patient in use. Optionally, the coating can include a third polymer which can include acrylamide, a photoreactive group, or both.

In another embodiment the invention provides a method for forming a lubricious coating on a medical device, including steps of disposing a coating composition comprising a first polymer that is an acrylic acid polymer, a second polymer that is an acrylamide copolymer comprising at least one photoreactive group, and a cross-linking agent comprising at least two photoreactive groups, on a medical device surface. Disposing can be done using a dip-coating method. In some modes of practice the coating is performed in at a pH of less than about 6, such as about pH 5, which beneficially increases the viscosity of the coating composition and provides advantages. The coating can then be treated with UV light to activate the photoreactive groups to cause bonding and formation of the coating. The form coating may also optionally be treated with a bicarbonate solution to provide salt groups on the coated surface.

In another embodiment the invention provides a method for performing a medical procedure using the coated medical device, which comprises a step of inserting the coated medical device in a subject, wherein the lubricious coating reduces the friction associated with moving the device in a portion of the body. Coatings of the invention advantageously provide very good lubricity and a low amount of particulate release when exposed to an aqueous environment, which is very desirable for in vivo use.

DETAILED DESCRIPTION

Figure 1:
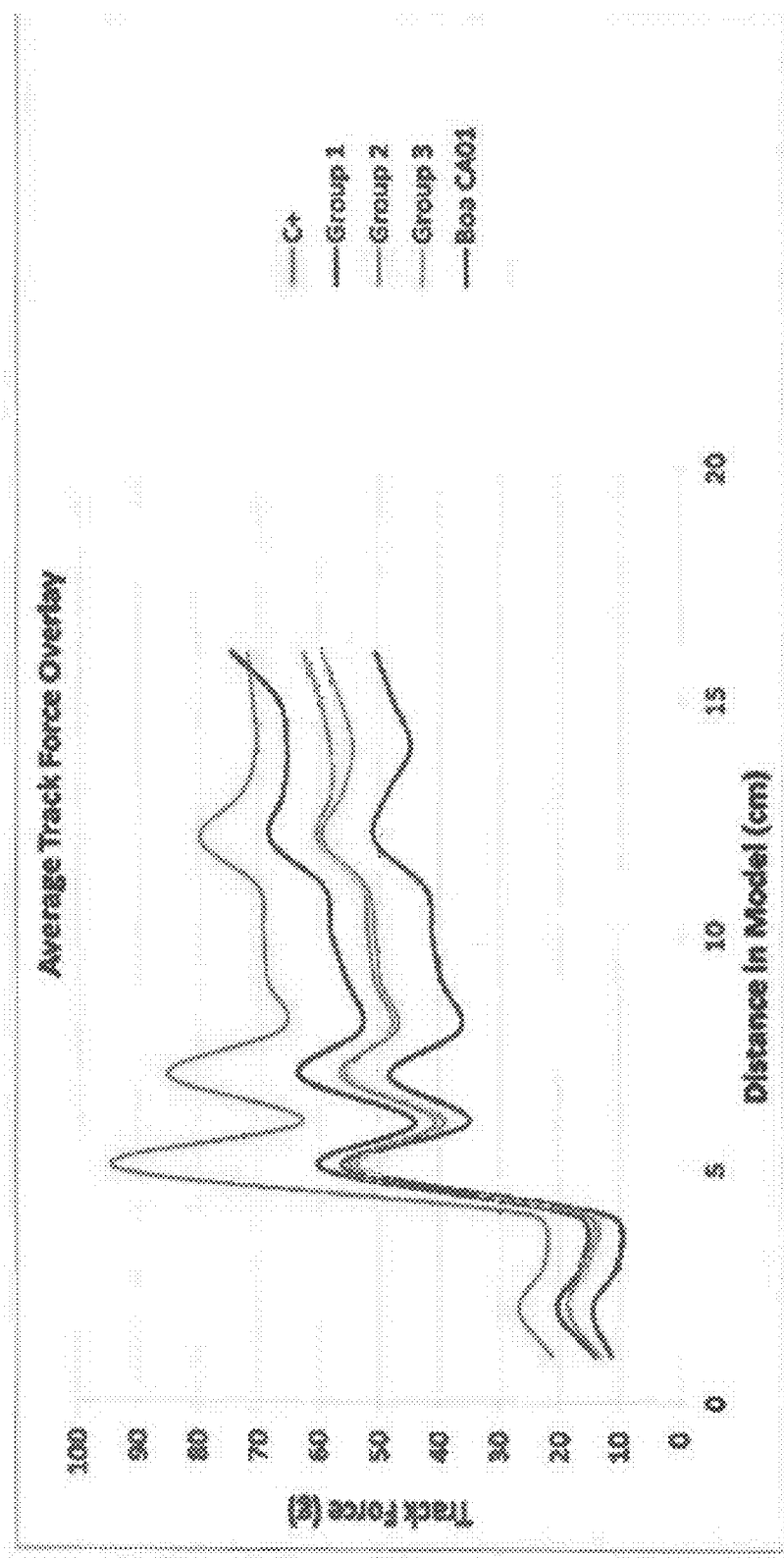
FIG. 1 is a graph showing track force (g) over length for different device coatings.
Figure 2:
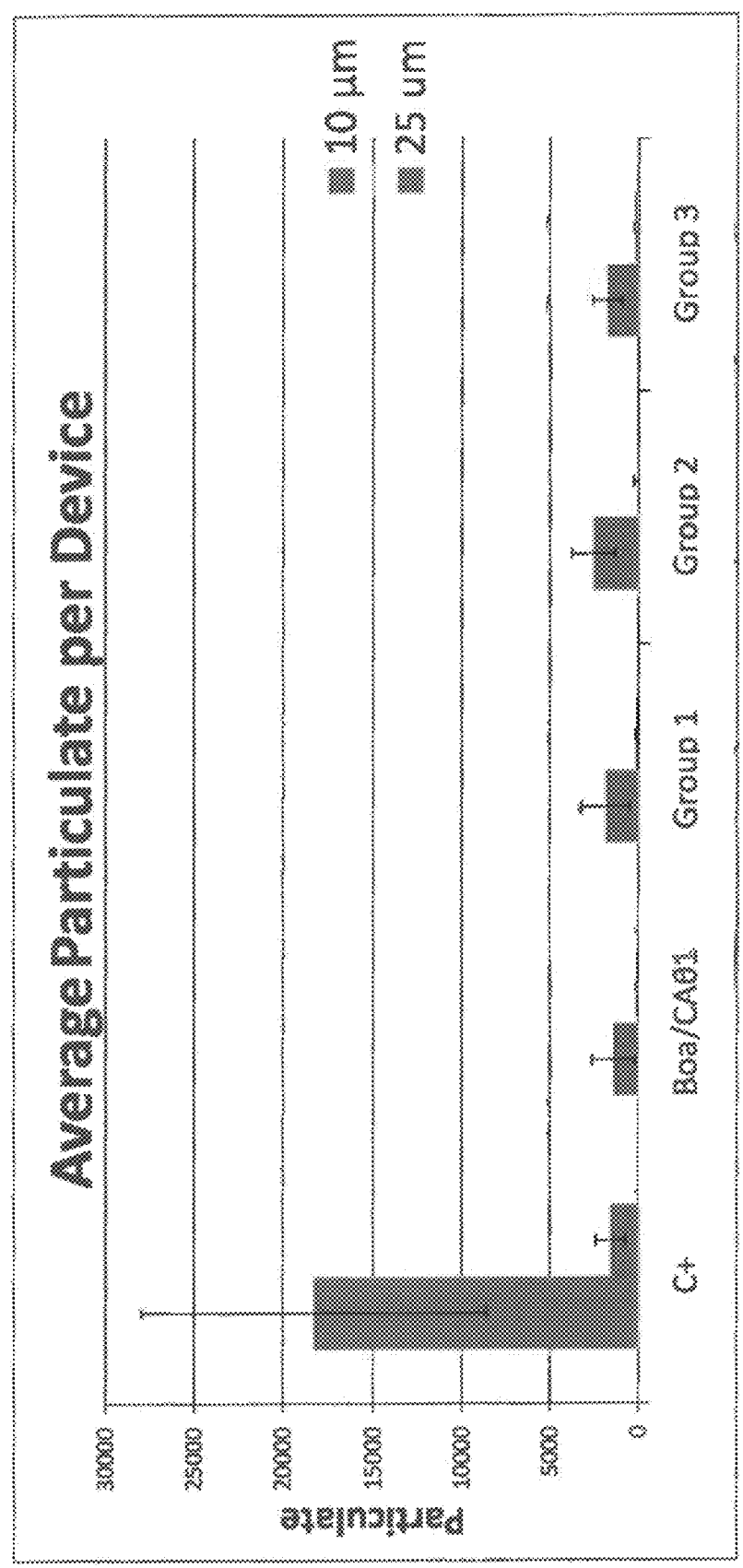
FIG. 2 is a graph showing average particulate counts (10 μm, 25 μm) for different device coatings.

The embodiments of the present disclosure described herein are not intended to be exhaustive or to limit the disclosure to the precise forms disclosed in the following detailed description. Rather, the embodiments are chosen and described so that others skilled in the art can appreciate and understand the principles and practices of the present disclosure.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, one approach to reducing the friction between a medical device and the environment surrounding the medical device is to apply a lubricious coating onto the medical device. However, many lubricious coatings are relatively ineffective in reducing the friction between the device and the environment surrounding the device (such as an intravascular space, as one example). In addition, many lubricious coatings lack sufficient durability leading to a rapid increase in friction during the course of use.

The coating can be present as a single coated layer on the device. The single layer can be described as the coating. Beneficially, and in some modes of practice, the coating can be formed using a single coating composition. For example, a coating composition can include the first polymer, second polymer, and crosslinking agent, wherein the coating composition is disposed on a device surface and treated to form the coating. As such, the coated layer is in contact with a medical device surface and also configured to contact a patient in use.

The coating of the disclosure includes an acrylic acid polymer (e.g., used as the "first polymer" in the coating composition). As used herein an "acrylic acid polymer" refers to polymers including acrylic acid monomeric units. The acrylic acid polymer can be an acrylic acid homopolymer or an acrylic acid copolymer including acrylic acid and one or more (e.g., two, three, four, five, etc.) other monomeric units that are different than acrylic acid.

In embodiments, in a poly(acrylic acid) copolymer, the acrylic acid can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater, 92.5% (mol) or greater, 95% (mol) or greater, 97.5% (mol) or 99% (mol) or greater. In exemplary embodiments, acrylic acid is present in the copolymer in the range of about 75% (mol) to about 99.99% (mol), about 85% (mol) to about 99.99% (mol), about 95% (mol) to about 99.99% (mol), or about 98% (mol) to about 99.99% (mol). In some embodiments, some or all of the acrylic acid groups of the polymer are in salt form. The polymer can be partially or fully salted by adding a base salt to a polymer composition, such as sodium hydroxide or potassium hydroxide.

An acrylic acid copolymer can include one or more co-monomers copolymerizable with acrylic acid. Exemplary co-monomers that can be used to prepare an acrylic acid copolymer include those that have a carboxylic acid group, such as methacrylic acid, itaconic acid, monomethyl itaconic acid, maleic anhydride, fumaric acid, and crotonic acid, and salts thereof. Other exemplary co-monomers include sulfonic acid-group containing monomers such as acrylamido-2-methylpropanesulfonic acid (AMPS), 2-(meth)acrylamido-2-methylpropane sulfonic acid, vinyl sulfonic acid, 2-sulfoethyl methacrylate, and salts thereof. Acrylic acid copolymers made from a combination of two or more different acid-group containing monomers can be used, or copolymers made from one or more acid-group containing monomers and one or more non-acid group containing monomers can be used. Acrylic acid copolymers can include random copolymers, block copolymers, graft copolymers, or blends thereof. Other exemplary carboxylic acid-containing monomers that can be used to prepare acrylic acid group-containing copolymers include styrene and maleic anhydride copolymerized to produce styrene-maleic anhydride copolymer (PSMA).

The acrylic acid polymer may optionally be described with reference to its pH. For example, the acrylic acid polymer may have a pH in the range of about 1 to about 5, about 1.2 to about 5, about 1.5 to about 5, about 2.5 to about 5, about 2.75 to about 4.5, or about 3 to about 4.25.

In some embodiments, the acrylic acid polymer can have an average molecular weight of 150 kDa or greater. In yet other embodiments the acrylic acid polymer can have an average molecular weight of 500 kDa or greater, 750 kDa or greater, or 1000 kDa or greater, such as in the range of about 1000 kDa to about 2500 kDa, about 1000 kDa to about 2000 kDa, or about 1000 kDa to about 2000 kDa.

In some modes of preparation, the acrylic acid polymer is prepared by free radical polymerization of acrylic acid at (e.g, about a 0.8 M concentration) in deionized water. In modes where a portion of the acid groups are neutralized, a concentrated base such as NaOH is added to the acrylic acid solution. Next, an initiator such as ammonium persulfate is added with stirring. The polymerization solution can be degassed with nitrogen and stirred for hours (e.g., 12-24 hours) at an elevated temperature (e.g., greater than 50° C.). The polymer can then be polymerized against continuous flow deionized water using 12-14 K dialysis tubing, and then isolated by lyophilization.

The coating also includes an acrylamide copolymer that has at least one photoreactive group (e.g., used as the "second polymer" in the coating composition). As used herein an "acrylamide polymer" refers to polymers including acrylamide or methacrylamide monomeric units, further including one or more pendent photoreactive groups from the acrylamide polymer backbone. In embodiments, the acrylamide copolymer can be an acrylamide homopolymer further modified to provide pendent photoreactive groups, or acrylamide co-polymer formed from the polymerization reaction of an acrylamide or methacrylamide monomer with one or more other comonomers, prepolymers, or mixtures thereof.

In embodiments, in an acrylamide polymer, acrylamide or methacrylamide is the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater in the copolymer. In exemplary embodiments, acrylamide or methacrylamide is present in the copolymer in the range of about 50% (mol) to about 99% (mol), about 75% (mol) to about 98% (mol), about 80% (mol) to about 97% (mol), or about 85% (mol) to about 95% (mol).

In embodiments, the acrylamide polymer includes one or more comonomers that include an acid group. Exemplary co-monomers with acid groups include sulfonic acid-group containing monomers such as acrylamido-2-methylpropane-sulfonic acid (AMPS), 2-(meth)acrylamido-2-methylpropane sulfonic acid, vinyl sulfonic acid, 2-sulfoethyl methacrylate, and salts thereof, and monomers that include a carboxylic acid group, such as methacrylic acid, itaconic acid, monomethyl itaconic acid, maleic anhydride, fumaric acid, and crotonic acid, and salts thereof. In embodiments, an acid group-containing copolymer can be present in the acrylamide copolymer (second polymer) in an amount in the range of about 0.1% (mol) to about 20% (mol), about 0.5% (mol) to about 15% (mol), or about 1% (mol) to about 10% (mol).

In embodiments, the acrylamide polymer includes one or more oxyalkylene monomers, or one or more segments of oxyalkylene polymer. For example, the acrylamide polymer can include one or more ethylene oxide and/or propylene oxide units. The acrylamide polymer can be formed from an oxyalkylene prepolymer having one or more reactive chemistries that can allow it to be incorporated to form an acrylamide copolymer. The oxyalkylene segment can be based on an ethylene glycol polymer or oligomer having the structure HO—$(CH_2-CH_2-O)_n$—H. As an example, the value of n ranges from about 3 to about 150 and the number average molecular weight (Mn) of the poly(ethylene glycol) ranges from about 250 Da to about 40 kDa, more typically ranging from about 300 Da to about 20 kDa, from about 400 Da to about 10 kDa, from about 500 Da to about 5000 Da, or about 600 Da to about 1000 Da. An oxyalkylene polymer can be effectively derivatized to add polymerizable groups to produce oxyalkylene based pre-polymers. Polymerizable groups such as glycidyl acrylate, glycidyl methacrylate, or acrylic or methacrylic acid can be reacted with the terminal hydroxyl groups of these polymers to provide terminal polymerizable groups.

Some specific examples of alkylene oxide polymer-based prepolymers that can be used to form the acrylamide polymer include, poly(propylene glycol)$_{540}$-diacrylate, poly(propylene glycol)$_{475}$-dimethacrylate, poly(propylene glycol)$_{900}$-diacrylate, poly(ethylene glycol)$_{250}$-diacrylate, poly(ethylene glycol)$_{575}$-diacrylate, poly(ethylene glycol)$_{550}$-dimethacrylate, poly(ethylene glycol)$_{750}$-dimethacrylate, poly(ethylene glycol)$_{700}$-diacrylate, and poly(ethylene glycol)$_{1000}$-diacrylate, poly(ethylene glycol)$_{2000}$ diacrylate, poly(ethylene glycol)$_{1000}$ monomethyl ether monomethacrylate, and poly(ethylene glycol)$_{500}$ monomethyl ether monomethacrylate. These types of alkylene oxide polymer-based macromers are available from Sigma-Aldrich (St. Louis, Mo.) or Polysciences (Warrington, Pa.).

In an acrylamide copolymer, oxyalkylene can be defined in terms of a molar amount in the polymer, or a weight percentage of the copolymer. When an oxyalkylene prepolymer is reacted with other monomers to form the acrylamide copolymer, it can be convenient to describe the amount of oxyalkylene by a weight percentage in the copolymer. In some embodiments the oxyalkylene is present in an amount in the range of about 0.5% (wt) to about 25% (wt), about 2% (wt) to about 20% (wt), or about 5% (wt) to about 15% (wt).

The acrylamide copolymer (second polymer) can also include a desired loading of photogroups. Reagents and methods for the preparation of an acrylamide copolymer with pendent photoreactive groups can be found in references such as U.S. Pat. Nos. 4,979,959; 5,002,582; 5,263,992; 5,414,075; 5,512,329; and 5,637,460, the teaching of which are incorporated herein by reference. In some modes of practice, an acrylamide copolymer with photoreactive groups can be formed by the copolymerization of acrylamide, 1-vinyl-2-pyrrolidone, and N-(3-aminopropyl(meth)acrylamide), optionally with one or more other copolymers or prepolymers, such as an oxyalkylene prepolymer. The resulting copolymer then can be derivatized with an acyl chloride (such as, for example, 4-benzoylbenzoyl chloride) under Schotten-Baumann conditions. That is, the acyl chloride reacts with the amino group of the N-(3-aminopropyl) moiety of the copolymer. An amide is formed resulting in the attachment of the aryl ketone to the polymer.

An acrylamide copolymer comprising a photoreactive group can also be prepared by copolymerizing acrylamide (and optionally with one or more other copolymers or prepolymers) with a monomer derivatized with a photoreactive group. Exemplary monomer derivatives include aryl ketone derivatives of hydrophilic free radically polymerizable monomers such as acrylamide, methacrylamide and AMPS. One exemplary methacrylamide-based monomer with a pendent photoreactive groups is N-[3-(4-benzoylbenzamido) propyl]methacrylamide (BBA-APMA), the synthesis which is described in Examples 1-3 of U.S. Pat. No. 5,858,653 (Duran et al.) Another exemplary methacrylamide-based monomer with a pendent photoreactive group is N-[3-(7-methyl-9-oxothioxanthene-3-carboxiamido)propyl] methacrylamide (MTA-APMA), the synthesis which is described in Examples 1-2 of U.S. Pat. No. 6,156,345 (Chudzik et al.)

In exemplary embodiments the second polymer comprises acrylamide-2-acrylamido-2-methylpropanesulfonate (AMPS)- and poly(ethylene glycol)-containing subunits, and further comprises pendent photogroups, as described herein.

Optionally, in some embodiments, the coating also includes a third polymer that is different than the first and second polymers. The third polymer can be another acrylamide copolymer, which also optionally can include photoreactive groups. In some embodiments the third polymer is an acrylamide copolymer comprising pendent photoreactive groups, but that does not include an oxyalkylene segment. In exemplary embodiments, the third polymer is an acrylamide copolymer, wherein acrylamide or methacrylamide is the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater in the copolymer. In exemplary embodiments, acrylamide or methacrylamide is present in the third polymer in the range of about 50% (mol) to about 99% (mol), about 75% (mol) to about 97% (mol), about 80% (mol) to about 100% (mol), or about 98% (mol) to about 100% (mol).

An exemplary third copolymer can be prepared by copolymerizing acrylamide, (e.g., 95-99% mol) with APMA (e.g., 1-5% mol) to form an acrylamide-APMA copolymer, and then reacting with an excess of 4-benzoylbenzoyl chloride in chloroform to provide pendent photoreactive groups.

In yet other embodiments the coating can include other biocompatible polymers. Such other biocompatible polymers can be used as the optional third polymer, or can be used as fourth, fifth, etc. polymer. Exemplary biocompatible include those that contain ether groups such as poly(ethylene oxide) (PEO), poly(propylene oxide) (PPO), poly(propylene glycol) (PPG) poly(vinyl methyl ether), polymeric alcohols such as poly(vinyl alcohol) (PVA), poly(2-hydroxyehtylacrylate) (PHEA) and poly(2-hydroxyethyl vinyl ether) PHEVE), poly(2-ethyl-2-oxazoline) (PEOX), poly(n-acetyl-iminoethylene) (PAIE) and water soluble polysaccharides such as methyl cellulose, hydroxypropylcellulose and hydroxyethylcellulose.

The coating composition also includes a crosslinking agent having two or more photoreactive groups, which can react with the polymers in the composition, the device surface, or both. Suitable photoreactive groups include aryl ketones, such as acetophenone, benzophenone, anthraquinone, anthrone, quinone, and anthrone-like heterocycles. A crosslinking agent including a photoreactive group can be referred to as a photo-crosslinker or photoactivatable crosslinking agent. The photoactivatable crosslinking agent can be ionic, and can have good solubility in an aqueous composition. Thus, in some embodiments, at least one ionic photoactivatable crosslinking agent can be used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable crosslinking agents include 4,5-bis(4-benzoylphenylmethyleneoxy) benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis [2-(4-benzoylbenzyloxy)ethyl]-2-aminoethanesulfonic acid or salt, and the like. See U.S. Pat. No. 6,077,698 (Swan et al.), U.S. Pat. No. 6,278,018 (Swan), U.S. Pat. No. 6,603,040 (Swan) and U.S. Pat. No. 7,138,541 (Swan) the disclosures of which are incorporated herein by reference.

Other exemplary ionic photoactivatable crosslinking agents include ethylenebis(4-benzoylbenzyldimethylammonium) dibromide and hexamethylenebis(4-benzoylbenzyldimethylammonium) dibromide and the like. See U.S. Pat. No. 5,714,360 (Swan et al.) the disclosures of which are incorporated herein by reference.

In yet other embodiments, restrained multifunctional reagents with photoactivable crosslinking groups can be used in association with device embodiments of the disclosure. In some examples these restrained multifunctional reagents include tetrakis (4-benzoylbenzyl ether) of pentaerthyritol and the tetrakis (4-benzoylbenzoate ester) of pentaerthyritol. See U.S. Pat. No. 5,414,075 (Swan et al.) and U.S. Pat. No. 5,637,460 (Swan et al.) the disclosures of which are incorporated herein by reference.

Crosslinking agents can include those having formula $Photo^1$-LG-$Photo^2$, wherein $Photo^1$ and $Photo^2$ independently represent at least one photoreactive group and LG represents a linking group comprising at least one silicon or at least one phosphorus atom. A degradable linking agent can include a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Pub. Pat. App. No. 2011/0144373 (Swan, et al.), the disclosure of which is incorporated herein by reference.

Crosslinking agents including at least two photoreactive groups can be used in association with coating embodiments of the disclosure. Exemplary crosslinking agents are described in U.S. Pat. No. 8,889,760, the content of which is herein incorporated by reference in its entirety.

In some embodiments, a crosslinking agent having a molecular weight of less than about 1500 kDa can be used in association with coating embodiments of the disclosure. In some embodiments the crosslinking agent can have a molecular weight of less than about 1200, 1100, 1000, 900, 800, 700, 600, 500, or 400.

In some embodiments, a crosslinking agent comprising a linking agent having formula Photo$^1$-LG-Photo$^2$ can be used in association with coating embodiments of the disclosure. Photo$^1$ and Photo$^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, device embodiments of the disclosure can be associated with a crosslinking agent comprising a linking agent having a formula selected from:

(a)

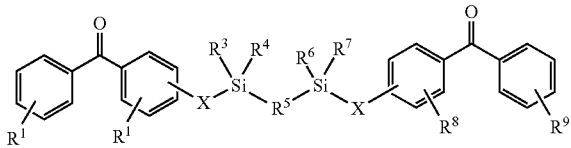

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

(b)

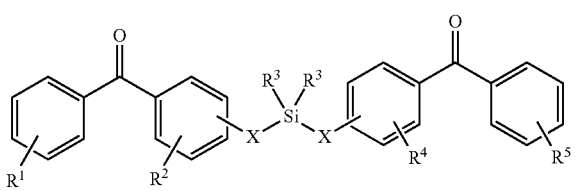

wherein R1 and R5 are any substitution; R2 and R4 can be any substitution, except OH; R3 can be alkyl, aryl, or a combination thereof; and X, independently, are O, N, Se, S, alkylene, or a combination thereof;

(c)

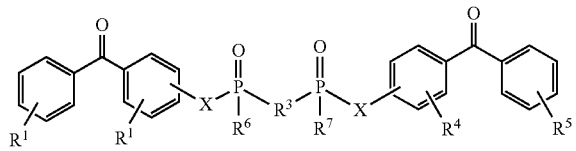

wherein R1, R2, R4 and R5 are any substitution; R3 is any substitution; R6 and R7 are alkyl, aryl, or a combination thereof; and each X can independently be O, N, Se, S, alkylene, or a combination thereof; and (d)

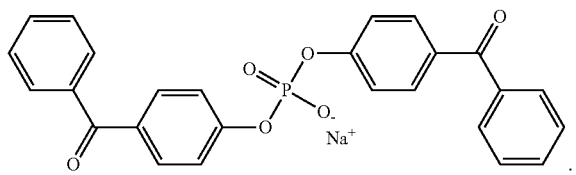

In a particular embodiment, the crosslinking agent can be bis(4-benzoylphenyl) phosphate.

In some embodiments, an ionic photoactivatable crosslinking agent having good solubility in an aqueous composition can be used in association with coating embodiments of the disclosure. Any suitable ionic photoactivatable crosslinking agent can be used. In some embodiments, the ionic photoactivatable crosslinking agent is a compound of formula I: $X_1$—Y—$X_2$ where Y is a radical containing at least one acidic group, basic group, or a salt of an acidic group or basic group. $X_1$ and $X_2$ are each independently a radical containing a latent photoreactive group. The photoreactive groups can be the same as those described herein. Spacers can also be part of $X_1$ or $X_2$ along with the latent photoreactive group. In some embodiments, the latent photoreactive group includes an aryl ketone or a quinone.

The radical Y in formula I provides the desired water solubility for the ionic photoactivatable crosslinking agent. The water solubility (at room temperature and optimal pH) is at least about 0.05 mg/mL. In some embodiments, the solubility is about 0.1 to about 10 mg/mL or about 1 to about 5 mg/mL.

In some embodiments of formula I, Y is a radical containing at least one acidic group or salt thereof. Such a photoactivatable crosslinking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic crosslinking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278, 018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; $X_1$ and $X_2$ can contain photoreactive groups that include aryl ketones. Such photoactivatable crosslinking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis(4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable crosslinking agent can be a compound having the formula:

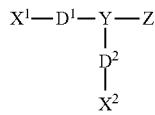

wherein $X^1$ includes a first photoreactive group; $X^2$ includes a second photoreactive group; Y includes a core molecule; Z includes at least one charged group; $D^1$ includes a first degradable linker; and $D^2$ includes a second degradable linker. Additional exemplary degradable ionic photoactivatable crosslinking agents are described in U.S. Patent Application Publication US 2011/0144373 (Swan et al., "Water Soluble Degradable Crosslinker"), the disclosure of which is incorporated herein by reference.

In some aspects a non-ionic photoactivatable crosslinking agent can be used. In one embodiment, the non-ionic photoactivatable crosslinking agent has the formula $XR_1R_2R_3R_4$, where X is a chemical backbone, and $R_1$, $R_2$, $R_3$, and $R_4$ are radicals that include a latent photoreactive group. Exemplary non-ionic crosslinking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable crosslinking agent can be represented by the formula:

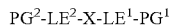

wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Other non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Exemplary non-ionic photoactivatable crosslinking agents can also include, for example, those described in U.S. Pat. Publication 2013/0143056 (Swan et al., "Photo-Vinyl Primers/Crosslinkers"), the disclosure of which is incorporated herein by reference. Exemplary crosslinking agents can include non-ionic photoactivatable crosslinking agents having the general formula $R^1—X—R^2$, wherein $R^1$ is a radical comprising a vinyl group, X is a radical comprising from about one to about twenty carbon atoms, and $R^2$ is a radical comprising a photoreactive group.

A single photoactivatable crosslinking agent or any combination of photoactivatable crosslinking agents can be used in forming a coating associated with device embodiments of the disclosure. For example, at least one nonionic crosslinking agent such as tetrakis(4-benzoylbenzyl ether) of pentaerythritol can be used with at least one ionic crosslinking agent. For example, at least one non-ionic photoactivatable crosslinking agent can be used with at least one cationic photoactivatable crosslinking agent such as an ethylenebis (4-benzoylbenzyldi-methylammonium) salt or at least one anionic photoactivatable crosslinking agent such as 4,5-bis (4-benzoyl-phenylmethyleneoxy)benzene-1,3-disulfonic acid or salt. In another example, at least one nonionic crosslinking agent can be used with at least one cationic crosslinking agent and at least one anionic crosslinking agent. In yet another example, a least one cationic crosslinking agent can be used with at least one anionic crosslinking agent but without a non-ionic crosslinking agent.

An exemplary crosslinking agent is disodium 4,5-bis[(4-benzoylbenzyl)oxy]-1,3-benzenedisulfonate (DBDS). This reagent can be prepared by combining 4,5-dihydroxylbenzyl-1,3-disulfonate (CHBDS) with 4-bromomethylbenzophenone (BMBP) in THF and sodium hydroxide, then refluxing and cooling the mixture followed by purification and recrystallization (also as described in U.S. Pat. No. 5,714,360, incorporated herein by reference).

Further crosslinking agents can include the crosslinking agents described in U.S. Pub. Pat. App. No. 2010/0274012 (to Guire et al.) and U.S. Pat. No. 7,772,393 (to Guire et al.) the content of which is herein incorporated by reference.

A coating associated with coating embodiments of the disclosure can include boron-containing linking agents such as boron-containing linking agents disclosed in U.S. Pat. Publication 2013/0302529 ("Boron-Containing Linking Agents;" Kurdyumov et al.), the content of which is herein incorporated by reference. By way of example, linking agents can include borate, borazine, or boronate groups and coatings and devices that incorporate such linking agents, along with related methods. In an embodiment, the linking agent includes a compound having the structure (I):

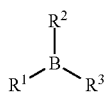 (I)

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group. In some embodiments the bonds B—$R^1$, B—$R^2$ and B—$R^3$ can be chosen independently to be interrupted by a heteroatom, such as O, N, S, or mixtures thereof.

Additional agents for use with device embodiments herein can include stilbene-based reactive compounds including, but not limited to, those disclosed in U.S. Pat. No. 8,487,137, entitled, "Stilbene-Based Reactive Compounds, Polymeric Matrices Formed Therefrom, and Articles Visualizable by Fluorescence" by Kurdyumov et al., the content of which is herein incorporated by reference.

Additional photoreactive agents, crosslinking agents, hydrophilic coatings, and associated reagents are disclosed in U.S. Pat. No. 8,513,320 (to Rooijmans et al.); U.S. Pat. No. 8,809,411 (to Rooijmans); and 2010/0198168 (to Rooijmans), the content of all of which is herein incorporated by reference.

The coating can include predetermined amounts of polymers to provide a lubricious coating.

In embodiments, the first polymer (acrylic acid polymer) is the primary polymer in the coating by weight, meaning that it is present in an amount by weight that is greater than any other polymer in the coating composition. For example, the first polymer (acrylic acid polymer) can be present in an amount by weight greater than the second polymer (acrylamide photopolymer), or the optional third polymer (e.g., another acrylamide polymer that is different than the second polymer), or present in an amount by weight greater than the combined amount of the first and second polymers. In some embodiments a combined amount of the second and third polymer by weight is approximately the same as the amount of the first polymer. In embodiments, the first and second polymers constitute about 90% (wt) or greater, 95% (wt) or greater, 98% (wt) or greater, or 100% (wt) of the polymeric materials of the coating composition, or of the total solids of the coating composition. In embodiments, the first, second, and third polymers constitute about 90% (wt) or greater, 95% (wt) or greater, 98% (wt) or greater, or 100% (wt) of the polymeric materials of the coating composition, or of the total solids of the coating composition.

In some embodiments the first polymer (acrylic acid polymer) is present in an amount in the range of about 20 to about 80% (wt), of about 30 to about 70% (wt), or about 40 to about 60% (wt), of the solids components in the coating composition. In some embodiments the second polymer (acrylamide photopolymer) is present in an amount in the range of about 10 to about 60% (wt), of about 20 to about 50% (wt), or about 30 to about 40% (wt) of the solids components in the coating composition. In some embodiments the optional third polymer (e.g., another acrylamide polymer that is different than the second polymer) is present in an amount in the range of about 1 to about 35% (wt), of about 5 to about 25% (wt), or about 10 to about 20% (wt) of the solids components in the coating composition. In some embodiment that the cross-linking agent is present in an amount in the range of about 0.1% to about 5% (wt), of about 0.5% to about 4% (wt), or about 0.75% to about 3% (wt) of the solids components in the coating.

In some modes of practice a coating solution is formed including the first polymer (acrylic acid polymer), second polymer (acrylamide photopolymer), the cross-linking agent, and optionally a third polymer (e.g., another acrylamide photopolymer that is different than the second polymer), in a solvent or mixture of solvents. In some embodiments, the solvent for the coating composition can include water, an alcohol, or a mixture of water an alcohol. An exemplary alcohol is isopropyl alcohol (IPA).

Exemplary mixtures of water to alcohol include those where the proportion of water to alcohol (vol:vol), such as IPA, is in the range of about 99:1 to about 95:5, in the range of about 95:5 to about 50:50, or in the range of about 90:10 to about 75:25.

In some modes of practice the pH of the solution is not greater than about 6, such as in the range of about 2 to about 6, or in the range of about 3 to about 5. The solution can be adjusted with a compound to provide the desired pH. As the coating composition includes the acrylamide polymer, this can increase the viscosity of the composition providing coating advantages. A more viscous coating composition can improve the coating process and permit a lower concentration of solids materials (polymers and crosslinker) in the coating composition, which provides economic as well as processing advantages.

In some embodiments, the viscosity of the coating composition is about 15 centipoise (cP) or greater, such as in the range of about 17 cP to about 200 cP.

Accordingly, in some modes of practice the concentration of solids in the composition is not greater than about 30 mg/mL, or not greater than about 25 mg/mL, such as in the range of about 5 mg/mL to about 30 mg/mL, or about 10 mg/mL to about 25 mg/mL.

The coating solution can be applied to a substrate. Prior to application of the first coating solution to the substrate, one or more of many different pretreatment steps can be taken. In some embodiments, the surface of the substrate can be cleaned. For example, the surface can be wiped or dipped into an alcohol such as isopropyl alcohol. In some embodiments, the substrate can be put into a detergent solution such as a VALTRON solution and sonicated. In some embodiments, a compound can be disposed on the surface of the substrate to act as a tie layer. In some embodiments the surface of the substrate can be sterilized.

Many different techniques can be used to apply the solution to the substrate. By way of example, exemplary techniques can include drop coating, blade coating, dip coating, spray coating, and the like. In various embodiments, the solution is applied by dip coating. A dip coating process can includes steps of placing the substrate to be coated in the coating composition, letting the substrate sit (dwell) in the coating composition for a period of time, and then withdrawing the substrate from the coating composition.

The dwell time can be very short, such as a second or seconds, or can be for longer periods of time, such as minutes. The speed of dip coating can vary. For example, the substrate can be dipped into the coating solution and then withdrawn at a speed in the range of about 0.01 to about 10 cm/s, in the range of about 0.1 to about 4 cm/s, or in the range of about 0.5 to about 2 cm/s.

After the coating solution is applied to the substrate, actinic radiation such as UV radiation, can be applied to activate photoreactive groups within the components of the coating solution forming the coating. Actinic radiation can be provided by any suitable light source that promotes activation of the photoreactive groups. Preferred light sources (such as those available from Dymax Corp.) provide UV irradiation in the range of 190 nm to 360 nm. An exemplary UV light source is a Dymax 2000-EC series UV flood lamp with a 400 Watt metal halide bulb. A suitable dose of radiation is in the range of from about 0.5 mW/cm$^2$ to about 2.0 mW/cm$^2$. Exemplary irradiation times are in the range of seconds to several minutes, such as about 30 seconds to about 2 minutes. Optionally, the coating solution can be dried, before or after application of the actinic radiation.

In some modes of practice, some or all of the pendent acid groups from the acrylic acid polymer in the coating are converted to their corresponding salts. This can be accomplished after the coating is treated with UV light, and then by subjecting the coating to bicarbonate treatment. After the coating is treated with UV light it can be subjected to bicarbonate treatment. In an exemplary bicarbonate method the coated device is immersed in an aqueous sodium bicarbonate solution for a period of time and dried until complete. Materials and methods for bicarbonate treatment of coatings can be found in the commonly assigned U.S. Provisional Application Ser. No. 62/272,440, entitled "Lubricious Coatings With Surface Salt Groups" filed Dec. 29, 2015, the teaching of which is incorporated herein by reference.

Substrates on which the coating can be formed can be partially or entirely fabricated from a metal, ceramic, glass, or the like, or a combination thereof. Substrates can include polymers such as polyurethanes and polyurethane copolymers, polyethylene, polyolefins, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate can be made of a single material, or a combination of materials.

Substrate polymers can also include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

In some embodiments, the substrate includes a polymer selected from the group consisting of polyamide, polyimide, polyether block amide (PEBAX), polyether ether ketone (PEEK), high density polyethylene (HDPE), polyethylene, polyurethane, and polyethylene vinyl acetate.

Metals that can be used as substrates in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

The methods and materials of the disclosure can be utilized to coat virtually any medical device for which it is desired to provide a lubricious coating on a surface. In particular, the coatings are particularly useful for medical articles that can be inserted into and moved within the body. Beneficially, the coating can be formed on many materials of the disclosure without requiring a primer layer, or requiring a separate top coat. As such, the coating composition with the first polymer, second polymer, and crosslinking agent, and optional third polymer, is in contact with a medical device surface and also configured to contact a patient in use.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff; sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products, vena cava filters, and embolic protection filters and devices and electrophysiology mapping and ablation catheters. In some embodiments coatings of the present disclosure can be used on exemplary medical devices such as braided catheters. In yet other embodiments the coatings can be used advantageously on braided catheters (e.g. PEBAX®).

In some aspects the coating is formed on a catheter selected from the group consisting of urethral catheters, renal catheters, intravenous catheters, artificial lung catheters, blood pressure and stent graft catheters, atherectomy catheters, clot extraction catheters, percutaneous transluminal coronary angioplasty (PTCA) catheters, drug infusion catheters, angiographic catheters, neurological catheters such as neurovascular balloon catheters, thoracic cavity suction drainage catheters, electrophysiology catheters, stroke therapy catheters, abscess drainage catheters, central venous access catheters, hemodialysis catheters, and parental feeding catheters.

In some embodiments, the thickness of the coating can be in the range of about 100 nm to about 5.0 µm, about 250 nm to about 5.0 µm, about 250 nm to about 1.0 µm, or about 1.0

μm to about 5.0 μm. The thickness can be determined using one or more technique, like microscopic techniques such as scanning electron micrography (SEM) or atomic force microscopy (AFM).

The coating can exhibit lubricity that may be observed as relative low friction. In some embodiments, the coating can be lubricious after exposure to water. The coating may exhibit lubricity of between 0 and 30 grams of force when wetted as measured by a vertical pinch test, such as that described below. In some embodiments, the coating may exhibit lubricity of less than about 20 grams of force when wetted. In some embodiments, the coating may exhibit lubricity of less than about 15 grams of force when wetted.

In various embodiments, the coating may be described in terms of durability of the lubricity. For example, the lubricity may be retained over an extended period of time when the coating is exposed to frictional forces. For example, in some embodiments, lubricity may be maintained over a plurality of frictional testing cycles. In some embodiments, the coating may exhibit a lubricity of between 0 and 30 grams of force when wetted for at least 10 consecutive testing cycles. In some embodiments, such as where at least 15 frictional test cycles are performed, the measured lubricity will increase no more than 30% between the average of cycles 1-5 and the average of cycles 10-15 of the testing.

The coating may exhibit a relatively low amount of particulate release when exposed to an aqueous environment. A medical device having a hydrophilic coating with low particulate levels is very desirable for in vivo use.

A description of particulate levels can be based on a predetermined coating area and thickness. In one mode of measurement the particle counts are based on 600 mm$^2$ of coated surface having a coating thickness in the range of 500 nm to 10 μm. However, it is understood that the particle count can be based on coating areas of greater or less than 600 mm$^2$. For example, the coating will generate less than 15,000 particles of greater than 10 microns in size in an aqueous environment. In some embodiments, the coating will generate less than 10,000 particles of greater than 10 microns in size in an aqueous environment. In some embodiments, the coating will generate less than 5,000 particles of greater than 10 microns in size in an aqueous environment. In some embodiments, the coating will generate less than 3,000 particles of greater than 10 microns in size in an aqueous environment. In some embodiments, the coating will generate less than 1,000 particles of greater than 10 microns in size in an aqueous environment. It will be appreciated that in accordance with various embodiments herein, the properties of lubricity and low particulate release are both present.

Testing of the particulates generated in aqueous solution for the examples herein was performed according to the following procedure. As a derivative of the procedures described in ASTM F2394, substrates were passed through a tortuous path in an aqueous solution.

Example 1

The following reagents, coating solutions, and substrates were used in generating the example.

PA-BBA-AMPS-PEG: N-Acetylated poly[acrylamide$^{93.6\%}$-co-sodium-2-acrylamido-2-methylpropane-sulfonate$^{4.9\%}$-co-N-(3-(4-benzoylbenzamido)propyl) methacrylamide$^{0.9\%}$]-co-methoxy poly(ethylene glycol)$_{1000}$ monomethacrylate$^{0.6\%}$ (percentages are mole percents) was obtained (PA-BBA-AMPS-PEG). Reagents and methods for the preparation of PA-BBA-AMPS-PEG, and Photo-PA can be found in references such as U.S. Pat. Nos. 4,979,959; 5,002,582; 5,263,992; 5,414,075; 5,512,329; and 5,637,460, the teachings of which are incorporated herein by reference.

BPP: The cross-linking agent sodium bis(4-benzoylphenyl) phosphate was prepared according to the methods described in U.S. Pub. No. 2012/0046384.

PAA: Poly(acrylic acid) having an average molecular weight in the range of 1200-1800 kDa was used.

Coating solution: A coating solution was prepared by mixing together PAA at 5 g/L; PA-BBA-AMPS-PEG at 3.5 g/L; photo-PA at 1.5 g/L; BPP at 0.15 g/L in a solvent of 15% isopropyl alcohol and 85% water.

Bicarbonate treatment: A bicarbonate treatment solution was prepared with 0.1 M NaHCO$_3$ in water. Substrates were dipped in the aqueous sodium bicarbonate solution for five seconds and dried until complete.

Test Substrate: PEBAX® tubes (I.D. 0.018" O.D. 0.039"; 72D) obtained from Medicine Lake Extrusion, Plymouth, Minn.; and Pebax/Nylon catheters (O.D. 0.039"; catalog No. 08BQ-3020A) obtained from Bavaria Medizin Technologie Argelsrieder Feld 8,D-82234, Weßling.

Dip coating: The coating solution was applied to the substrate using a dip coat method. The substrate was immersed in the base coat coating solution with a dwell time of 2 seconds. The substrate was then extracted from the solution at a speed of 1.2 cm/s. The base layer was then air dried for 2 minutes.

Irradiation: The coating was then UV cured. Specifically, the coated substrate was rotated in front of a Dymax 2000-EC series UV flood lamp with a 400 Watt metal halide bulb for 60 seconds, approximately 20 cm from the light source.

Bicarbonate treatment: The coating solution was applied to the substrate using a dip coat method. The substrate was immersed in the sodium bicarbonate solution with a dwell time of 5 seconds. The substrate was then extracted from the solution at a speed of 1.2 cm/s. The base layer was then air dried for at least 10 minutes.

Friction (Lubricity) and Durability Testing Method: The coated substrates of the examples were evaluated for lubricity/durability by friction measurements using a Vertical Pinch Method, as described in International Application Number WO 03/055611 with the following modifications. The coated substrate samples were hydrated in phosphate-buffered saline (PBS, pH 7.4) for ≥1 minute and then inserted into the end of a rod holder, which was placed between the two jaws of a pinch tester and immersed in a cylinder of PBS. The jaws of the pinch tester were closed as the sample was pulled in a vertical direction for 10 cm at a travel rate of 1 cm/sec and opened when the coated sample was returned to the original position. A 500 g force was applied as the coated substrates were pulled up through the pinched jaws. The pull force exerted on the substrate was then measured (grams). Pull force (g) is equal to the coefficient of friction (COF) multiplied by pinch force (g). The apparatus used for the vertical pinch test method is described in U.S. Pat. No. 7,348,055, the content of which is herein incorporated by reference.

Particulate Testing Method: Testing of the particulates generated in aqueous solution for the examples herein was performed according to the following procedure. As a derivative of the procedures described in ASTM F2394, substrates were passed through a tortuous path in an aqueous solution described as follows. The distal portion of a 6 French guide catheter (Vista Brite Tip, Cordis) was cut off and discarded so that the catheter was 30 cm long. The guide catheter was inserted into the ASTM F2394-07 model. A hemostasis valve connector (Qosina) was attached to the guide catheter. The model was cleaned by flushing 120 mL Isoton (Becton, Dickinson, and Company) using a 60 mL syringe and discarding the flush. A base line flush with 120 mL Isoton was analyzed by light obscuration to determine background level of particulates. 90-cm tubes (1 mm diameter) with 20 cm coated were hydrated in Isoton for ≥1 minute. The tubes were inserted into the guide catheter and advanced until the distal portion of the rod exited the model. A 120 mL flush with Isoton was performed and collected in a glass beaker. The collected Isoton was immediately analyzed by light obscuration for particulates ≥10 microns. The tube was removed, and the model was cleaned with 120 ml Isoton and the next coated rod was tested.

What is claimed is:

1. A medical device comprising a lubricious coating comprising:
    an insertable medical article having an article surface upon which the lubricious coating is formed;
    a coated layer comprising a first polymer that is an acrylic acid polymer, a second polymer that is an acrylamide copolymer comprising at least one photoreactive group, a cross-linking agent comprising at least two photoreactive groups, and a third polymer that is different than the second polymer and is an acrylamide copolymer with at least one photo reactive group, wherein the second polymer comprises an oxyalkylene segment and the third polymer does not comprise an oxyalkylene segment,
    wherein the first polymer is present in an amount in the range of 20 to 80% (wt), and the second polymer is present in an amount in the range of 10 to 60% (wt) of solids components in the coating,
    wherein the coated layer is in contact with the insertable medical article surface and also configured to contact a patient in use, and
    wherein the medical device is configured to be inserted into, and removed from, a patient.

2. The medical device of claim 1, wherein the acrylic acid polymer has an average molecular weight of 150 kDa or greater.

3. The medical device of claim 1, wherein the acrylic acid polymer is an acrylic acid homopolymer.

4. The medical device of claim 1 wherein the second polymer comprises acrylamide-2-acrylamido-2-methylpropanesulfonate (AMPS)- and poly(ethylene glycol)-containing subunits.

5. The medical device of claim 1, wherein the second polymer, the third polymer, or both second and third polymer are present in an amount less than the first polymer.

6. The medical device of claim 1, wherein first polymer is present in an amount in the range of 30 to 70% (wt), the second polymer is present in an amount in the range of 20 to 50% (wt), and the third polymer is present in an amount in the range of 5 to 25% (wt), of solids components in the coating.

7. The medical device of claim 6, wherein first polymer is present in an amount in the range of 40 to 60% (wt), the second polymer is present in an amount in the range of 30 to 40% (wt), and the third polymer is present in an amount in the range of 10 to 20% (wt), of the solids components in the coating.

8. The medical device of claim 1, wherein the cross-linking agent is present in an amount in the range of 0.1% to 5% (wt) of the solids components in the coating.

9. The medical device of claim 1 wherein the cross-linking agent is a compound of a formula selected from:

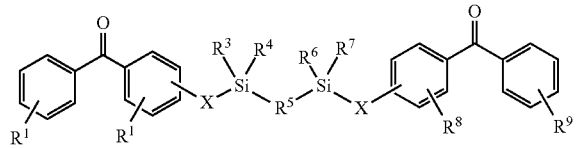

(a)

wherein $R^1$, $R^2$, $R^8$ and $R^9$ are any substitution; $R^3$, $R^4$, $R^6$ and $R^7$ are alkyl, aryl, or a combination thereof; $R^5$ is any substitution; and each X, independently, is O, N, Se, S, or alkyl, or a combination thereof;

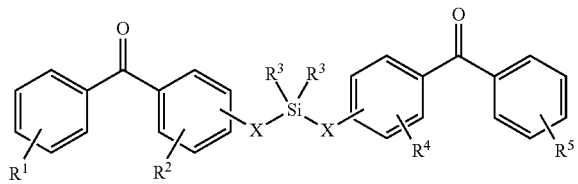

(b)

wherein $R^1$ and $R^5$ are any substitution; $R^2$ and $R^4$ can be any substitution, except OH; $R^3$ can be alkyl, aryl, or a combination thereof; and each X, independently, is O, N, Se, S, alkyl or a combination thereof;

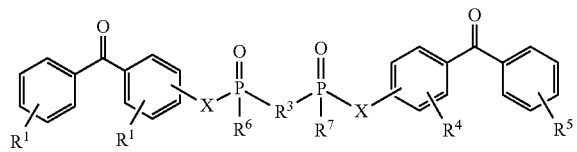

(c)

wherein $R^1$, $R^2$, $R^4$ and $R^5$ are any substitution; $R^3$ is any substitution; $R^6$ and $R^7$ are alkyl, aryl, or a combination thereof; and each X, independently, is O, N, Se, S, alkyl, or a combination thereof; and

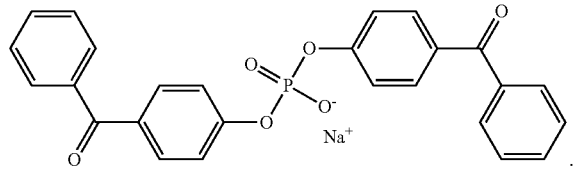

(d)

10. The medical device of claim 9 wherein at least one of the cross-linking agents is sodium bis(4-benzoylphenyl) phosphate.

11. The medical device of claim 1, wherein the article surface comprises a substrate material selected from the group consisting of polyamide, polyimide, polyether block amide (PEBAX), polyether ether ketone (PEEK), high density polyethylene (HDPE), polyethylene, polyurethane, or polyethylene vinyl acetate.

12. The medical device of claim 1, wherein the insertable medical article comprises a catheter.

13. The medical device of claim 1 wherein the coated layer releases less than 3,000 particles having a size greater than 10 microns per 600 mm² of coated layer, under the test conditions of ASTM F2394.

14. The medical device of claim 1, wherein the coated layer is formed from a liquid coating composition comprising the first polymer that is the acrylic acid polymer, the second polymer that is the acrylamide copolymer comprising at least one photoreactive group, and the cross-linking agent comprising at least two photoreactive groups, wherein the liquid coating composition has a pH of less than 6.

15. The medical device of claim 1, wherein the coated layer is contacted with a liquid composition comprising sodium bicarbonate.

16. The medical device of claim 1, wherein the coated layer has a thickness of 10.0 µm or less.

17. The medical device of claim 1, wherein the coated layer has a thickness in the range of 100 nm to 5.0 µm.

18. The medical device of claim 1 where, in the first polymer that is the acrylic acid polymer, acrylic acid is present in an amount of 95% (mol) or greater.

19. The medical device of claim 1 where, in the second polymer that is the acrylamide polymer, acrylamide or methacrylamide is present in an amount of 50% (mol) or greater.

20. The medical device of claim 1 where the first polymer is the primary polymer in the coated layer by weight.

21. The medical device of claim 1 which is formed by a process comprising applying a coating composition comprising the first polymer, the second polymer, the third polymer, and the cross-linking agent to an uncoated surface of the insertable medical article, and treating the coating composition to form the coated layer.

22. A method for treating a patient comprising inserting the medical device of claim 1 into a patient.

23. A medical device comprising a lubricious coating comprising:
    an insertable medical article having an article surface upon which the lubricious coating is formed;
    a coated layer comprising:
    a first polymer that is an acrylic acid homopolymer, or an acrylic acid copolymer consisting of acrylic acid and one or more monomers selected from the group consisting of methacrylic acid, itaconic acid, monomethyl itaconic acid, maleic anhydride, fumaric acid, and crotonic acid, acrylamido-2-methylpropanesulfonic acid (AMPS), 2-(meth)acrylamido-2-methylpropane sulfonic acid, vinyl sulfonic acid, 2-sulfoethyl methacrylate, and salts thereof, wherein acrylic acid is present in the copolymer in an amount of 95% (mol) or greater,
    a second polymer that is an acrylamide copolymer comprising at least one photoreactive group, wherein acrylamide or methacrylamide is present in an amount of 50% (mol) or greater in the second polymer,
    a third polymer that is different than the second polymer and is an acrylamide copolymer with at least one photo reactive group, wherein the second polymer comprises an oxyalkylene segment and the third polymer does not comprise an oxyalkylene segment, and
    a cross-linking agent comprising at least two photoreactive groups, and
    wherein the coated layer is in contact with the medical article surface and also configured to contact a patient in use.

* * * * *